(12) United States Patent
Croizat et al.

(10) Patent No.: US 11,123,473 B2
(45) Date of Patent: Sep. 21, 2021

(54) CONNECTION DEVICE FOR USE IN THE NEGATIVE PRESSURE THERAPY OF WOUNDS

(71) Applicant: PAUL HARTMANN AG, Heidenheim (DE)

(72) Inventors: Pierre Croizat, Herbrechtingen (DE); Axel Eckstein, Heidenheim (DE); Juergen Hofstetter, Heidenheim (DE); Swen Loeffler, Neustadt/Coburg (DE)

(73) Assignee: Paul Hartmann AG, Heidenheim (DE)

( * ) Notice: Subject to any disclaimer, the term of this patent is extended or adjusted under 35 U.S.C. 154(b) by 655 days.

(21) Appl. No.: 15/781,770

(22) PCT Filed: Dec. 7, 2016

(86) PCT No.: PCT/EP2016/080073
§ 371 (c)(1),
(2) Date: Jun. 6, 2018

(87) PCT Pub. No.: WO2017/097834
PCT Pub. Date: Jun. 15, 2017

(65) Prior Publication Data
US 2018/0361038 A1    Dec. 20, 2018

(30) Foreign Application Priority Data

Dec. 9, 2015   (DE) .................. 10 2015 224 746.5

(51) Int. Cl.
*A61M 1/00*   (2006.01)

(52) U.S. Cl.
CPC ............ *A61M 1/90* (2021.05); *A61M 1/0058* (2013.01); *A61M 1/86* (2021.05)

(58) Field of Classification Search
CPC . A61M 1/0088; A61M 1/0086; A61M 1/0058
See application file for complete search history.

(56) References Cited

U.S. PATENT DOCUMENTS 9,586,000 B2    3/2017   Eckstein et al.
2010/0268179 A1   10/2010   Kelch et al.
(Continued)

FOREIGN PATENT DOCUMENTS

CN    102686263 A    9/2012
CN    102711857 A    10/2012
(Continued)

OTHER PUBLICATIONS

International Search Report and Written Opinion from PCT/EP2016/080073 dated Mar. 6, 2017 with English Translation of International Search Report provided.
(Continued)

*Primary Examiner* — Tatyana Zalukaeva
*Assistant Examiner* — Jessica R Arble
(74) *Attorney, Agent, or Firm* — Dilworth & Barrese, LLP (57) ABSTRACT

The invention relates to a connection device (2) for use in the negative pressure therapy of wounds, comprising a flexible conducting means (6) and a connecting body (4) made of an elastomeric flexible material which can be applied to a negative pressure dressing which covers the wound and seals the wound off from the atmosphere, wherein the connecting body (4) has a centrally arranged raised first area (8) which receives the conducting means (6), and a flatter flange-shaped second area (10) opposite the first area, which second area forms a contact plane (12) on the negative pressure dressing, wherein a conducting portion (46) which is closed on all sides and is formed by the central first area adjoins a free end of the delivery lumen (42) of the conducting means (6) which opens in the central first area, wherein said conducting portion first opens at a distal end into an interior (16) of the central first area (8) and from there is in fluid communication with the suction lumen (40)

(Continued)

of the conducting means (6), characterized in that the central first area (8) has one single contiguous opening (20) which opens towards the negative pressure dressing in the contact plane (12), such that the at least one suction lumen (40) communicates with the wound space through said contiguous opening (20), and that extensions (22) integral with the first area (8) and extending in the contact plane (12) with free ends protrude into said contiguous opening (20) and form a means for preventing penetration of dressing or wound inlay materials sucked out of the wound space.

19 Claims, 4 Drawing Sheets

(56) References Cited

U.S. PATENT DOCUMENTS

| | | | |
|---|---|---|---|
| 2011/0152800 A1* | 6/2011 | Eckstein | A61M 1/0088 604/319 |
| 2011/0178481 A1 | 7/2011 | Locke et al. | |
| 2013/0066284 A1 | 3/2013 | Croizat et al. | |
| 2014/0031735 A1 | 1/2014 | Zurovcik | |
| 2014/0046281 A1* | 2/2014 | Eckstein | A61M 1/0088 604/313 |
| 2014/0066868 A1 | 3/2014 | Freedman et al. | |
| 2014/0121615 A1 | 5/2014 | Locke et al. | |
| 2015/0018786 A1 | 1/2015 | Locke et al. | |
| 2015/0359951 A1* | 12/2015 | Andersen | A61F 13/00068 604/319 |

FOREIGN PATENT DOCUMENTS

| | | |
|---|---|---|
| CN | 103917204 A | 7/2014 |
| CN | 104853785 A | 8/2015 |
| DE | 102012214178 A1 | 6/2014 |
| WO | 2014066057 A1 | 5/2014 |

OTHER PUBLICATIONS

German Search Report.
1st Chinese Office Action with English Translation from parallel Chinese Patent Application No. 201680081459.6 dated May 8, 2020.

* cited by examiner

CONNECTION DEVICE FOR USE IN THE NEGATIVE PRESSURE THERAPY OF WOUNDS

This application claims priority to German Patent Application No. 10 2015 224 746.5 filed on Dec. 9, 2015.

The invention relates to a connection device for use in the negative pressure therapy of wounds, with a flexible conducting means which can be subjected to negative pressure and to fluid media and has at least two lumina, and with a connecting body connected non-releasably to the conducting means, wherein at least one lumen is provided as suction lumen for subjecting to negative pressure, and at least one lumen is provided as delivery lumen for delivering a fluid medium, wherein the connecting body is made of an elastomeric flexible material and can be applied to a negative pressure dressing which covers the wound and seals the wound off tightly from the atmosphere, wherein the conducting means, during operation of the connection device, communicates with the wound space through the connecting body and through at least one opening in the negative pressure dressing, wherein the connecting body has a centrally arranged and raised first region, which receives the conducting means, and a flange-shaped second region which extends continuously in a circumferential direction about the first region, is flatter compared to the latter and forms a contact plane, and by means of which the connecting body can be placed flat against an upper side of the negative pressure dressing facing away from the wound, either directly or with interposition of adhesion promoters, and can be joined sealingly thereto, wherein a conducting portion which is closed on all sides and is formed by the central first region adjoins a free end of the delivery lumen of the conducting means opening into the central first region, which conducting portion opens only at a distal end into an interior of the central first region and from there is in fluidic communication with the suction lumen of the conducting means.

Negative pressure therapy of wounds, in particular of wounds which are deep and whose healing is therefore problematic a priori, has recently grown in importance. Negative pressure therapy means that a region of the body or a wound that would otherwise be exposed to the surrounding atmosphere is closed off in a pressure-tight manner or a negative-pressure-tight manner from the environment, that is to say from the atmosphere in which we live and breathe, by means of a dressing, wherein a pressure that is reduced with respect to the atmospheric pressure, which is therefore a negative pressure with respect to the atmosphere, is applied and continuously or intermittently maintained within the sealed wound region. Where mention is made of negative pressure in the field under discussion here, this is understood to mean a pressure range of typically between 0 and 250 mmHg (mm of mercury) below the ambient atmospheric pressure. It has been shown that this is conducive to wound healing. For the negative-pressure-tight closure of the wound, a negative pressure dressing is provided which, for example, can comprise a pressure-tight or vacuum-tight film layer, which is typically adhesively bonded to an intact body region surrounding the wound, thereby providing a tight seal. In order to supply a negative pressure to the wound space and maintain it there using a negative pressure generator, i.e. a vacuum pump in the broadest sense, the systems under discussion here for the negative pressure therapy of wounds can have conducting means to which a negative pressure can be applied and which interact with the negative pressure dressing by means of a connection device in order to apply a vacuum on or in the wound space.

A connection device of the type mentioned at the outset is known from DE 10 2012 214 178 A1. Despite this, connection devices have been proposed in large numbers in the past years. In the design of such connection devices, there is a degree of conflict in the sense that, on the one hand, the connection device is to be produced from a flexible and resilient material in order to provide a high level of comfort, while on the other hand it must be ensured, under all operating conditions and loads, that the connection device and its lumen carrying the negative pressure or the media are not compressed in such a way that communication, i.e. delivery and removal of fluid media, no longer functions in the intended manner. In this respect, embodiments have also been proposed in which the connection device has a three-dimensional structure above the contact plane, which greatly reduces the danger of a lumen being pressed shut and of the functional ability of the connection device thus being adversely affected, since stronger walls can be provided. On the other hand, this is associated with a considerable reduction in wearing comfort. In other connection devices with a very flat structure, an interior of the connection device had to be configured with a very limited space, or numerous support elements in the form of projections and ribs had to be provided in the interior and extended between a wall of the connection device facing toward the wound and a wall of the connection device facing away from the wound. Accordingly, a plurality of relatively small openings are provided in the wall of the connecting body facing the wound in order to communicate with the wound space.

The object of the present invention is to further improve a connection device of the type mentioned at the outset, specifically in such a way that negative-pressure communication is reliably ensured even under difficult conditions, wherein furthermore the danger of the inlet openings or of the interior of the connection device becoming blocked is not increased and is indeed reduced.

In a connection device of the type mentioned at the outset, this object is achieved according to the invention in that the central first region has one single continuous opening which leads toward the negative pressure dressing in the contact plane, which opening connects the interior of the central first region to the at least one opening in the negative pressure dressing, such that the at least one suction lumen communicates with the wound space through this continuous opening, and in that extensions integral with the first region and extending in the contact plane protrude with free ends into this continuous opening and form a means for preventing penetration of dressing materials or wound inlay materials aspirated from the wound space.

Preferably, the connecting body, including the extensions formed integrally therewith and protruding into the continuous opening, and preferably also the conducting means are made of PVC. In tests carried out by the applicant, PVC was found to be an advantageous compromise between inherent stability and comfortable resilience and deformability of the material.

With the present invention, it was found that, particularly when carrying out a rinsing process, i.e. when fluid rinsing media are conveyed through an instillation port to the connecting body and aspirated back out from there, or when large amounts of wound exudate are aspirated into the connecting body, there is a considerable danger that dressing materials or wound inlay materials are also aspirated and cause blockages in the interior of the connecting body. This danger is increased further by supports inside the interior of the connecting body. In order to reduce the danger of such materials penetrating into the connecting body, it has previously been the practice to form rather small openings in the contact plane of the connecting body. In this way, however, the flow cross section is in turn reduced. With the present invention, it is proposed by contrast to provide a single opening which is accordingly more extensive in surface area and is continuous in the contact plane, and which opening is much less inclined to be pressed shut or closed. In order to counter the problem of materials from the wound space penetrating into the connecting body, it is further proposed that extensions protrude into this continuous opening and form a means for preventing penetration of dressing materials or wound inlay materials that are aspirated from the wound space. These extensions are formed integrally with the flexible material of the connecting body, have a flat configuration and, viewed orthogonally with respect to the contact plane, are preferably finger-shaped and in particular substantially parallel to one another. Although the clear cross-sectional surface area of the opening is again slightly reduced by these extensions, there is overall nevertheless a large passage area available for communication of negative pressure and of media between the wound space and the interior of the connecting body, wherein said problem of blockage caused by penetrating materials can be substantially reduced by the extensions protruding into this opening.

In a further embodiment of the invention, it proves advantageous if the extensions extend by at most 80%, in particular by at most 70%, in particular by at most 60% and more particularly by at most 50% of the dimension of the opening in the direction of the respective extension. The extensions, which for their part are preferably finger-shaped or at any rate follow a recognizable direction, are thus at a distance from the boundary of the opening in this direction. Between the free end of the respective projection and the boundary of the opening, there is therefore an extensive clear passage area which permits good communication of negative pressure and media.

It moreover proves advantageous if extensions extend in the manner of a comb, i.e. starting from one side of the opening boundary and in particular parallel to one another and, as has been mentioned above, are spaced apart from the opposite opening boundary, such that a continuous region that is not limited by extensions is formed there.

It moreover proves advantageous if the surface area of the extensions in the contact plane has at most 60%, in particular at most 50%, in particular at most 40% and more particularly at most 35% of the surface area enclosed by the continuous opening, including the surface area of the extensions.

The thickness of the extensions, viewed orthogonally with respect to the contact plane, can advantageously be from 1 to 3 mm.

It moreover proves advantageous that the extensions can deflect in an elastically flexible manner with respect to the contact plane. They are thus able to deflect transversely or orthogonally with respect to this contact plane, specifically in the direction of the wound, for example for delivery of instillation fluid in the direction of the wound, or into the interior of the connecting body, for example on account of a strong volumetric flow subsequent to a rinsing or instillation process or at the start of negative pressure treatment, if the negative pressure is first built up as far as the wound space.

According to a further inventive concept, it proves advantageous if the deflection of the extensions is limited by the extensions bearing on an inner side of a wall, facing away from the wound, of the first central region. For this purpose, it proves advantageous if the inner side of the wall facing away from the wound has a rib, extending into the interior in the direction of the wound, or at least one projection against which the extensions can be placed. In this way, it is sufficient if, in the interior of the central first region of the connecting body, a projection is provided only above the extensions in order to stabilize the interior, in the event that pressure is applied to the connecting body from outside.

It is also proposed that the connecting body and the continuous opening which opens out in the contact plane are configured such that this opening has a clear passage area (i.e. without the surface area of the extensions) of 30% to 60% of the surface area of the central first region projected onto the contact plane.

With regard to a flat structural shape, it proves advantageous if the central first region is approximately cuboid, preferably with rounded corners and edges, wherein the shortest edge of the cuboid shape extends orthogonally with respect to the flange-shaped second region. Its length preferably measures at most 7 mm, wherein the length and width of the other edges lie preferably between 20 mm and 50 mm, in particular between 20 mm and 40 mm.

It moreover proves advantageous if the connecting body is composed of a single integrally produced injection molding, which forms the central first region and the flange-shaped second region. The entire connecting body is thus formed from one and the same injection-molded, elastically resilient material, preferably PVC.

However, it can have additional adhesive layers or application systems (described in more detail below) for negative-pressure-tight adhesion to the outside of a negative pressure dressing facing away from the wound.

It moreover proves advantageous if the first and/or second region is transparent. The second flange-shaped region preferably has a thickness of 0.5 to 1.5 mm orthogonally with respect to the contact plane.

The central first region has a height above the flange-shaped second region, in a direction orthogonal to the contact plane, of at most 12 mm, in particular of at most 7 mm, with a maximum dimension in the contact plane of at most 50 mm, in particular of at most 35 mm.

According to a further inventive concept, it proves particularly advantageous if the conducting means outside the central first region is not joined to the flange-shaped second region, such that the conducting means, on account of its flexibility, can be deflected in a hinged manner relative to the central first region, without considerable forces thereby being transmitted to the flange-shaped second region, which forces could adversely affect the join to the negative pressure dressing.

As has already been indicated, it proves advantageous if the connecting body is already provided with an application system by the manufacturer. For this purpose, it proves advantageous if, on the side of the flange-shaped second region facing away from the wound, or on the side of the flange-shaped second region facing toward the wound, the connecting body non-releasably supports a securing film which protrudes radially outward over a peripheral edge of the flange-shaped second region by at least 5 mm, in particular by at least 10 mm, and, on its side facing toward the wound, it has an adhesive layer by means of which it can be applied adhesively to the negative pressure dressing. If the securing film is applied on the side of the flange-shaped second region facing away from the wound, then it also adheres with its adhesive layer to this flange-shaped second region. It proves advantageous here if the securing film has, on the side facing toward the wound, at least one releasable protective film portion, and, on the side facing away from the wound, it has at least one supporting film portion, which is detachable after the connection device has been applied to the negative pressure dressing.

The invention also relates to a method for producing a connection device, said method having the features of claim 19.

Moreover, protection is claimed for a system for negative pressure therapy of wounds, with the components and features of claim 20.

Further features, details and advantages of the invention will become clear from the attached claims, from the drawing, and from the following description of a preferred embodiment of the invention.

Figures 1A, 1B:
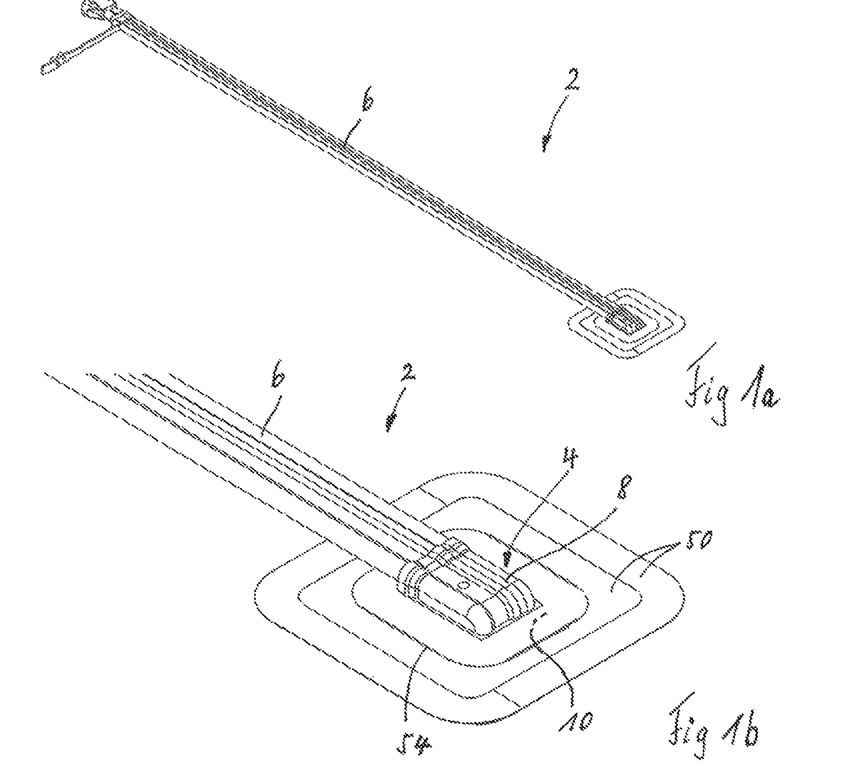
FIGS. 1a and 1b show perspective views of a connection device according to the invention with an application system.
Figure 5:
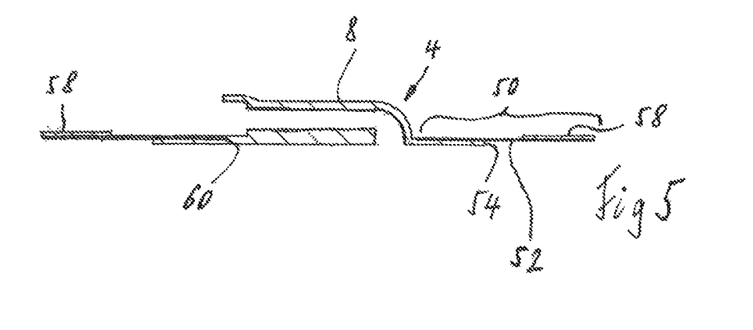
FIG. 5 shows a sectional view through the connecting body according to FIG. 4e, but with application system.

The figures show a connection device according to the invention, designated overall by reference sign 2, for use in the negative pressure therapy of wounds. The connection device 2 comprises a connecting body 4 which can be applied adhesively and preferably non-releasably to a negative pressure dressing (not shown) which covers the wound and seals it off tightly from the atmosphere, and a conducting means 6 connected non-releasably to the connecting body 4. The conducting means 6 provides negative-pressure communication or fluidic communication between the interior of the connecting body 4 and a negative pressure generator or a further conducting means leading to the latter. The negative-pressure communication or fluidic communication with the wound takes place through an opening (to be described below) in the connecting body and an opening in the negative pressure dressing covering the wound. The connection device 2 shown in FIGS. 1a and 1b moreover has an application system 50 joined to the side of the connecting body 4 facing away from the wound, which application system 50 is described with reference to FIG. 5 and is initially omitted below.

Figures 2A, 2B:
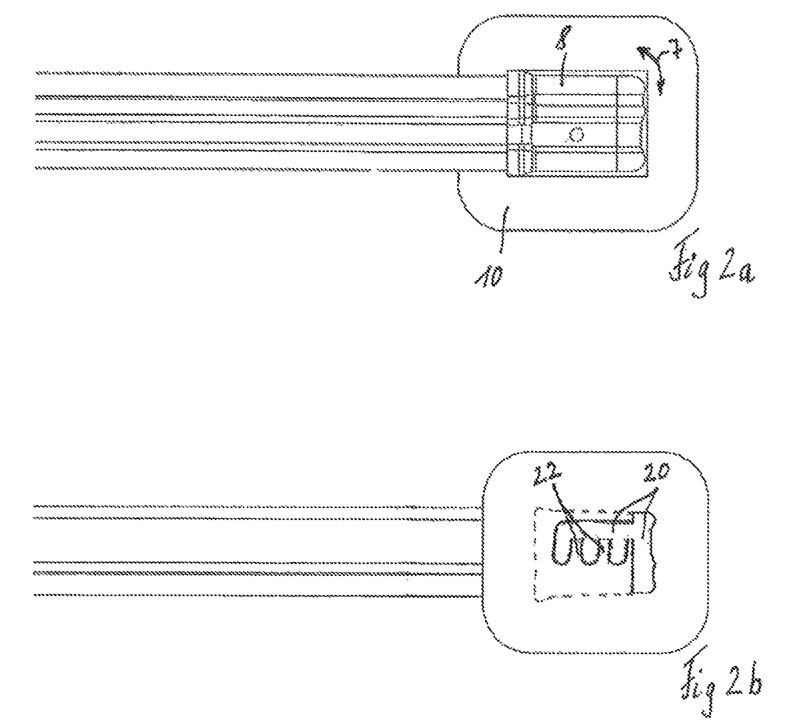
FIG. 2a shows a plan view of the connection device from FIGS. 1a and 1b without application system.
FIG. 2b shows a bottom view of the connection device from FIG. 2a, looking at a contact plane facing toward the wound.
Figure 2C:
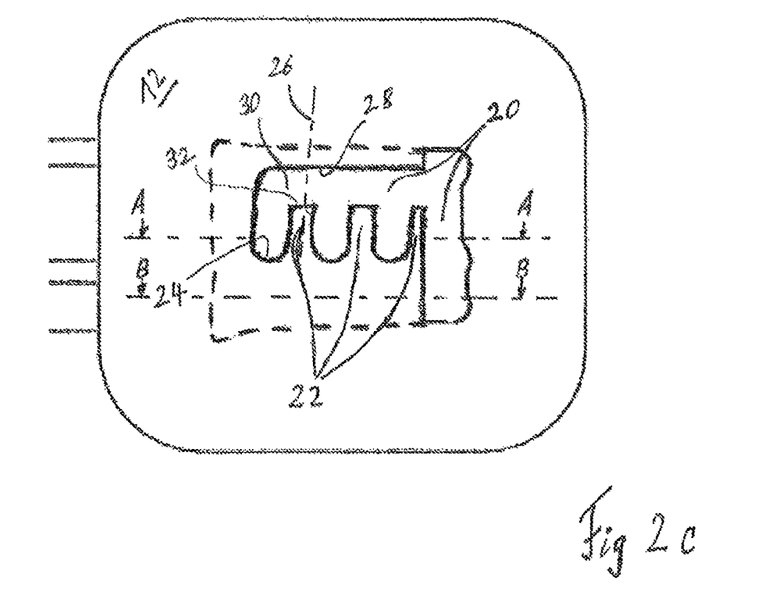
FIG. 2c shows an enlarged view of FIG. 2b.

The connecting body 4 comprises a central first region 8, which receives the conducting means 6 in a manner to be described below, and a flange-shaped second region which extends continuously in a circumferential direction 7 about the first region 8 and is flatter compared to the latter. The flange-shaped second region forms a contact plane 12 (FIG. 2b) by means of which the connecting body 4 can be placed flat against and fixed on the outer side of the negative pressure dressing facing away from the wound. The central first region 8 and the flange-shaped second region 10 are produced integrally as an injection molding from the same material. The central first region 8 rises a few millimeters from the side 14 of the flange-shaped second region 10 facing away from the wound. It is approximately cuboid, for example, although equally very flat. It comprises an interior 16 (FIG. 4) which is bounded at the top by a wall 18 facing away from the wound and which, toward the wound, leads through a single continuous opening 20 in the contact plane 12 in the direction of the wound and through the opening in the negative pressure dressing that covers the wound. A plurality of finger-shaped extensions 22 protrude into this continuous opening 20 of the connecting body 4. In the case shown as a preferred example, the finger-shaped extensions 22 extend approximately parallel to one another, starting from a side 24 delimiting the opening 20. The extensions 22 have a direction of extent 26 as indicated in FIG. 2c. In this direction 26, they are spaced apart from the opposite side 28 of the opening 20. Therefore, although the finger-shaped extensions 22 protrude into the opening 20 and end freely there, a large and clear passage area is nevertheless formed in the region 30 between a respective free end 32 of the projections 22 and the opposite side 28 or boundary of the opening 20. The finger-shaped extensions 22 are elastically resilient and deflectable relative to the contact plane 12 of the connecting body 4. They form a means for preventing penetration of dressing materials or wound inlay materials, for example foam, gauze or the like.

When the finger-shaped extensions 22 are deflected into the interior 16 of the central first region 8, they can be placed onto a projection 34 which protrudes in the direction of the wound, from the wall 18 facing away from the wound, wherein this projection 34 thus limits the deflectability of the finger-shaped extensions 22. This projection 34 is particularly configured in the form of a single rib extending in a longitudinal direction of the conducting means 6.

Figure 3A:
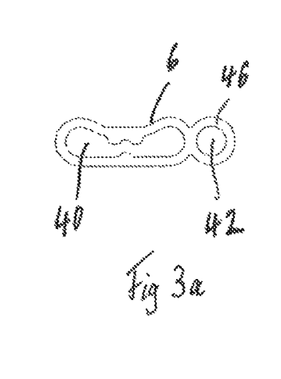
FIGS. 3a and 3b show a sectional view of the conducting means and a plan view of the conducting means of the connection device according to the invention.
Figure 3B:
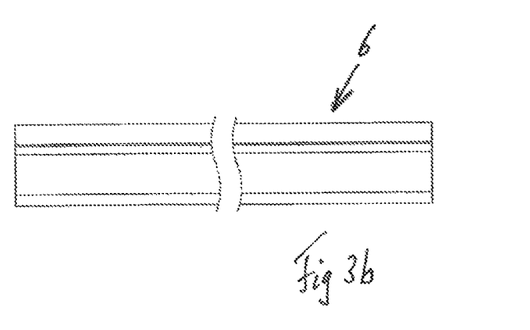
Figure 4A:
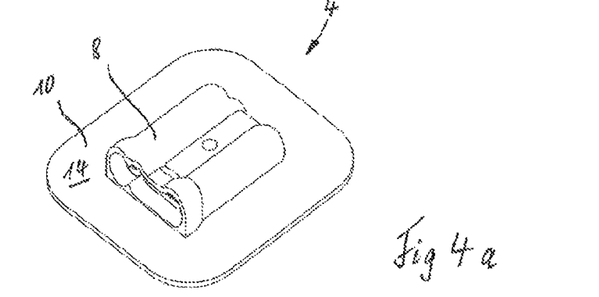
FIGS. 4a and 4b show perspective views of a connecting body of the connection device according to the invention.
Figure 4B:
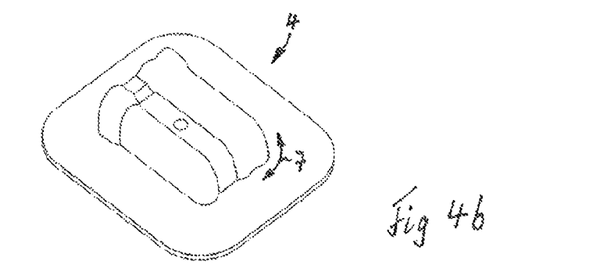
Figure 4C:
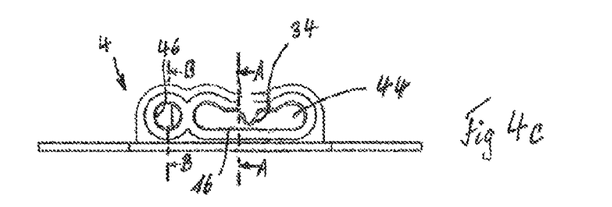
FIG. 4c shows a view of the connecting body, looking toward an insertion opening for the conducting means.
Figure 4D:
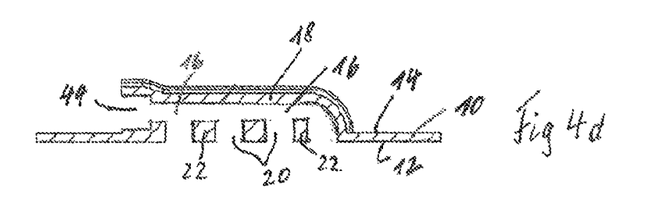
FIGS. 4d and 4e show sectional views through the connecting body along sectional planes A-A and B-B in FIGS. 2b and 4c, respectively.
Figure 4E:
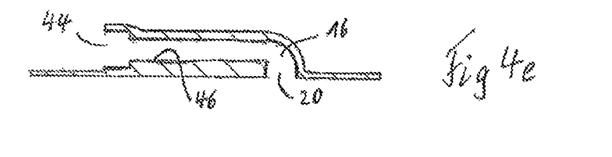

The interior 16 of the central first region 8 communicates, on the one hand, with the wound space via the described opening 20 and, on the other hand, with at least one suction lumen 40 and at least one delivery lumen 42 of the conducting means 6 (FIG. 3a). For connection of the conducting means 6 to the central first region 8 by the manufacturer, an insertion opening 44 is formed there which opens out parallel to the contact plane 12 and which corresponds to the outer contour of the conducting means 6. The conducting means 6 is insertable with its free end into the insertion opening 44 and is fixed there by cohesive bonding, and preferably non-releasably for the intended use, and in a negative-pressure-tight manner. The suction lumen 40 leads into the interior 16 of the central first region 8. By contrast, a conducting portion 46 which is closed on all sides and is formed by the central first region 8 adjoins a free end of the delivery lumen 42 of the conducting means 6, which conducting portion 46 extends in the longitudinal direction through the central first region 8 and opens only at the opposite end into the interior 16. It proves advantageous that the continuous opening 20 is also formed in the region of the distal end of this conducting portion 46, such that instillation liquid delivered there is able to pass into the wound space. If rinsing liquid is delivered into the interior 16 through the delivery lumen 42, it proves advantageous that the rinsing liquid is introduced into the interior 16 on the opposite side of the insertion opening 44 for the conducting means 6.

The application system 50 already mentioned at the outset comprises a thin securing film 52 which protrudes radially outward beyond a peripheral edge 54 of the connecting body 4 and, on its side facing toward the wound, has an adhesive layer (not shown) which is covered by detachable and mutually overlapping protective film portions (not shown). Moreover, on the side facing away from the wound, a shape-stabilizing supporting film portion 58 is provided which is detached after the connection device 2 has been applied to the negative pressure dressing. The securing film 52 is transparent, which is why the contour and the peripheral edge 54 of the flange-shaped second region 10 can be seen in FIG. 1*b*.

The securing film 52 preferably has an opening 60 with which it can be pushed over the central first region 8 as long as the conducting means 6 is not yet inserted into the connecting body 4, and it can be applied adhesively on the side 14 of the flange-shaped second region 10 facing away from the wound. The conducting means 10 is thereafter inserted into the insertion opening 44 and fixed sealingly.

The invention claimed is:

1. A connection device (2) for use in the negative pressure therapy of wounds, with a flexible conducting means (6) which can be subjected to negative pressure and to fluid media and has at least two lumina, and with a connecting body (4) connected non-releasably to the conducting means (6), wherein at least one lumen is provided as a suction lumen (40) for subjecting to negative pressure, and at least one lumen is provided as a delivery lumen (42) for delivering a fluid medium, wherein the connecting body (4) is made of an elastomeric flexible material and can be applied to a negative pressure dressing which covers the wound and seals the wound off tightly from the atmosphere, wherein the conducting means (6), during operation of the connection device, communicates with the wound space through the connecting body (4) and through at least one opening in the negative pressure dressing, wherein the connecting body (4) has a centrally arranged and raised first region (8), which receives the conducting means (6), and a flange-shaped second region (10) which extends continuously in a circumferential direction (7) about the first region (8), is flatter compared to the first region (8) and forms a contact plane (12), and by means of which the connecting body (4) can be directly placed flat against an upper side of the negative pressure dressing facing away from the wound, and can be joined sealingly thereto, wherein a conducting portion (46) which is closed on all sides and is formed by the central first region adjoins a free end of the delivery lumen (42) of the conducting means (6) opening into the central first region, which conducting portion (46) opens only at a distal end into an interior (16) of the central first region (8) and from there is in fluidic communication with the suction lumen (40) of the conducting means (6), characterized in that the central first region (8) has one single continuous opening (20) which leads toward the negative pressure dressing in the contact plane (12), which opening (20) connects the interior (16) of the central first region (8) to the at least one opening in the negative pressure dressing, such that the suction lumen (40) communicates with the wound space through this continuous opening (20), and in that extensions (22) integral with the first region (8) and extending in the contact plane (12) protrude with free ends into this continuous opening (20) and form a means for preventing penetration of dressing materials or wound inlay materials aspirated from the wound space, and wherein the extensions (22), viewed orthogonally with respect to the contact plane (12), are finger-shaped.

2. The connection device of claim 1, wherein the connecting body (4) is made of PVC.

3. The connection device of claim 1, wherein the extensions (22) extend by at most 80%, of the dimension of the opening (20) in a direction (26) of the respective extension (22).

4. The connection device of claim 1, wherein the extensions (22) extend in the manner of a comb starting from one side (24) of the opening (20).

5. The connection device of claim 1, wherein the surface area of the extensions (22) in the contact plane (12) is at most 60% of the surface area enclosed by the continuous opening (20), and the surface area of the extensions (22).

6. The connection device of claim 1, wherein the extensions (22) have a thickness of 1 to 3 mm orthogonal to the contact plane (12).

7. The connection device of claim 1, wherein the extensions (22) can deflect in an elastically flexible manner with respect to the contact plane (12).

8. The connection device of claim 7, wherein the deflection of the extensions (22) is limited by the extensions (22) bearing on an inner side of a wall (18), facing away from the wound, of the first central region.

9. The connection device of claim 8, wherein the inner side of the wall (18) facing away from the wound has a rib, extending into the interior (16) in the direction of the wound, or at least one projection (34) against which the extensions (22) can be placed.

10. The connection device of claim 1, wherein the continuous opening (20), which opens out in the contact plane (12), has a clear passage area of 30-60% of the surface area of the central first region (8) projected onto the contact plane.

11. The connection device of claim 1, wherein the central first region (8) is approximately cuboid, wherein the shortest edge of the cuboid shape extends orthogonally with respect to the flange-shaped second region.

12. The connection device of claim 1, wherein the connecting body (4) is composed of a single integrally produced by injection molding, which forms the central first region (8) and the flange-shaped second region (12).

13. The connection device of claim 1, wherein the first and/or second region (8, 10) is transparent.

14. The connection device of claim 1, wherein the central first region (8) has a height above the flange-shaped second region (10), in a direction orthogonal to the contact plane (12), of at most 12 mm, with a maximum dimension in the contact plane (12) of at most 50 mm.

15. The connection device of claim 1, wherein the conducting means (6) outside the central first region (8) is not joined to the flange-shaped second region (10), such that the conducting means, on account of its flexibility, can be deflected in a hinged manner relative to the central first region (8), without considerable forces thereby being transmitted to the flange-shaped second region (10).

16. The connection device of claim 1, wherein on the side of the flange-shaped second region (10) facing away from the wound, or on a side (14) of the flange-shaped second region (10) facing toward the wound, the connecting body (4) non-releasably supports a securing film (52) which protrudes radially outward over a peripheral edge (54) of the flange-shaped second region (10) by at least 5 mm, and, on its side facing toward the wound, it has an adhesive layer by means of which it can be applied adhesively to the negative pressure dressing.

17. The connection device of claim 16, wherein the securing film (52) has, on the side facing toward the wound, at least one releasable protective film portion, and, on the side facing away from the wound, it has at least one supporting film portion (58), which is detachable after the connection device has been applied to the negative pressure dressing.

18. A method for producing the connection device of claim 1, wherein the connecting body (4) with central first region (8) and with flange-shaped second region (10) is produced and supplied in one piece, and in that a securing film (52), extending in the circumferential direction (7) and having a central recess (60), is provided on the side of the flange-shaped second region (10) facing away from the wound, the securing film (52) being pushed with its central recess (60) over the central first region (8), after which the securing film (52) then adheres non-releasably by means of adhesive to the side (14) of the flange-shaped second region (10) facing away from the wound for the intended use and protrudes outward beyond a peripheral edge (54) of the flange-shaped second region (10), and in that the conducting means (6) is thereafter inserted into an opening (44) of the first central region (8) opening out approximately parallel to the contact plane (12) and is secured by cohesive bonding and in a negative-pressure-tight manner.

19. A system for negative pressure therapy of wounds, with an appliance which comprises a negative pressure generator and which has a negative pressure port and a rinsing or instillation port, comprising the connection device (2) of claim 1, wherein the suction lumen (40) of the conducting means (6) is fluidically connected to the negative pressure port and the delivery lumen (42) of the conducting means (6) is fluidically connected to the rinsing or instillation port.

* * * * *